(12) United States Patent
Didriksen et al.

(10) Patent No.: US 6,753,013 B1
(45) Date of Patent: Jun. 22, 2004

(54) PHARMACEUTICAL COMPOSITION

(75) Inventors: Erik Didriksen, Ballerup (DK); Gert Høy, Ballerup (DK)

(73) Assignee: Leo Pharmaceutical Products, Ltd. A/S, Ballerup (DK)

( * ) Notice: Subject to any disclaimer, the term of this patent is extended or adjusted under 35 U.S.C. 154(b) by 0 days.

(21) Appl. No.: 09/959,367

(22) PCT Filed: Jan. 27, 2000

(86) PCT No.: PCT/DK00/00033
§ 371 (c)(1),
(2), (4) Date: Oct. 22, 2001

(87) PCT Pub. No.: WO00/64450
PCT Pub. Date: Nov. 2, 2000

(30) Foreign Application Priority Data

Apr. 23, 1999 (DK) ......................... 1999 00561

(51) Int. Cl.⁷ ........................ A61K 9/14; A61K 31/59; A61K 31/56; A61K 31/44; A61K 31/41
(52) U.S. Cl. ................. 424/484; 424/485; 424/486; 424/487; 424/488; 514/167; 514/178; 514/336; 514/384
(58) Field of Search ................. 514/167, 178, 514/336, 384, 383; 424/484–488

(56) References Cited

U.S. PATENT DOCUMENTS

| | | | |
|---|---|---|---|
| 4,569,935 A | * | 2/1986 | Rosenberg et al. |
| 4,794,106 A | * | 12/1988 | Takashima et al. |
| 4,981,845 A | * | 1/1991 | Pereira |
| 5,087,620 A | | 2/1992 | Parab |
| 5,827,520 A | * | 10/1998 | de Salvert |
| 5,854,246 A | * | 12/1998 | Francois et al. |
| 5,886,038 A | | 3/1999 | Glenn et al. |
| 5,990,100 A | | 11/1999 | Rosenberg et al. |

FOREIGN PATENT DOCUMENTS

| | | |
|---|---|---|
| EP | 0 129 003 | 12/1984 |
| EP | 0 544 391 | 6/1993 |
| WO | WO 91/12807 | 9/1991 |
| WO | WO 94/14453 | 7/1994 |
| WO | WO 94/15912 | 7/1994 |

OTHER PUBLICATIONS

Ruzick et al.., British Journal of Dermatology 1998; 139: 254–258.*
CAPlus AN: 1985:27554 English abstract of Veverka, CS 214078, 1982.*
Gennaro Remington's Pharmaceutical Sciences, 18th ed., p. 1310.*
Kragballe et al., British Journal of Dermatology, vol. 139, pp. 649–654 (1998).
Richards et al., J. Am. Acad Dermatol., vol. 41, No. 4, pp. 581–583 (Oct. 1999).
Bazek et al., Nouv. Dermatol., vol. 13, No. 10, pp. 746–751 (1994) (with English translation).
"Database STN Intern. File Caplus [On line]; Glade C P et al: Epidermal cell DNA content and intermediate filaments keratin 10 and vimentin after treatment of" retrieved from CAPLUS, accession No. 1996:599855. Database accession No. 125:266250 XP002900974 abstract * BR. J. Dermatol., vol. 135, No. 3, 1996, pp. 379–384.
Ruzicka et al: "Comparison of calcipotriol monotherapy and a combination of calcipotriol and betamethasone valerate after 2 weeks'treatment with calcipotriol in the topical therapy of psoriasis vulgaris: a multicentre, doucle–blind, randomized study" British Journal of Dermatology, vol. 138, 1998, pp. 254–258, XP002900975 pp. 257.

* cited by examiner

Primary Examiner—Sreeni Padmanabhan
Assistant Examiner—San-ming Hui
(74) Attorney, Agent, or Firm—Birch, Stewart, Kolasch & Birch, LLP

(57) ABSTRACT

A pharmaceutical composition for dermal use, wherein the composition has a first pharmacologically active component A consisting of at least one vitamin D or vitamin D analogue, and a second pharmacologically active component B consisting of at least one corticosteroid, wherein the difference between the maximum stability pH of said first component A and the maximum stability pH of said second component B is at least 1. The composition can also have at least one solvent component C, where component C is compounds of the general formula $R^3(OCH_2C(R^1)H)_xOR^2$ (I), wherein x is in the range of 2–60, $R^1$ in each of the x units independently is H or $CH_3$, $R^2$ is straight chain or branched $C_{1-20}$alkyl or benzoyl, and $R^3$ is H or phenylcarbonyloxy; di-(straight or branched)-$C_{4-10}$alkyl esters of $C_4$–$C_8$dicarboxylic acids; straight or branched $C_{12-18}$-alkyl benzoates; straight or branched $C_{2-4}$-alkyl esters of straight or branched $C_{10-18}$-alkanoic or -alkenoic acids; propyleneglycol diesters with $C_{8-14}$-alkanoic acids; and branched primary $C_{18-24}$alkanols.

23 Claims, 4 Drawing Sheets

Percentage change in PASI score at each visit and end of treatment

| Percentage change in PASI score | COMB (n=301) | CALC (n=308) | BETA (n=312) | VEHICLE (n=107) |
|---|---|---|---|---|
| Visit 1 | | | | |
| Mean | 10.9 | 10.9 | 10.7 | 10.6 |
| Percentage change | | | | |
| To visit 2 | | | | |
| Mean | -48.1 | -28.4 | -41.4 | -21.5 |
| To visit 3 | | | | |
| Mean | -64.9 | -40.8 | -53.2 | -27.4 |
| To visit 4 | | | | |
| Mean | -73.9 | -51.3 | -64.5 | -31.3 |
| To end of treatment | | | | |
| Mean | -73.2 | -48.8 | -63.1 | -28.8 |

FIGURE 2

Investigator's assessment of overall Efficacy at each visit and end of treatment

| Investigator's overall efficacy assessment | COMB (n=301) % | CALC (n=308) % | BETA (n=312) % | VEHICLE (n=107) % |
|---|---|---|---|---|
| Visit 2 | | | | |
| Non responder | 63.5 | 89.5 | 72.5 | 98.1 |
| Responder | 36.5 | 10.5 | 27.5 | 1.9 |
| Total | 100.0 | 100.0 | 100.0 | 100.0 |
| Visit 3 | | | | |
| Non responder | 41.5 | 82.2 | 62.7 | 94.2 |
| Responder | 58.5 | 17.8 | 37.3 | 5.8 |
| Total | 100.0 | 100.0 | 100.0 | 100.0 |
| Visit 4 | | | | |
| Non responder | 23.1 | 64.4 | 42.4 | 91.9 |
| Responder | 76.9 | 35.6 | 57.6 | 8.1 |
| Total | 100.0 | 100.0 | 100.0 | 100.0 |
| End of treatment | | | | |
| Non responder | 23.9 | 66.6 | 44.2 | 92.5 |
| Responder | 76.1 | 33.4 | 55.8 | 7.5 |
| Total | 100.0 | 100.0 | 100.0 | 100.0 |

FIGURE 4

PHARMACEUTICAL COMPOSITION

This application is the National Phase of International Application PCT/DK00/00033 filed Jan. 27, 2000 which designated the U.S. and that International Application

FIELD OF THE INVENTION

The present invention concerns pharmaceutical compositions for dermal use which contain at least one vitamin D or vitamin D analogue and at least one corticosteroid. More specifically, the invention relates to pharmaceutical compositions containing two or more pharmacologically active compounds which have low compatibility with respect to the pH value of optimum stability, preferably, said pharmacologically active compounds are at least one vitamin D analogue and at least one corticosteroid.

BACKGROUND OF THE INVENTION

In the treatment of a number of conditions using dermal application, e.g. in the art treatment of psoriasis, it is often indicated to employ a combination treatment incorporating two or even more different pharmacologically active compounds. Thus, in the treatment of e.g. psoriasis, it is common to use a combination treatment involving a steroid compound, such as a corticosteroid compound, and a vitamin D analogue such as calcipotriol, and where each of the active compounds are formulated in separate preparations.

Until now a topical pharmaceutical composition comprising a combination of a vitamin D analogue and a topical steroid has not been described. Moreover, these two types of compounds often have optimum stability values of pH that differ significantly from one another making it non-obvious to attempt to prepare a topical pharmaceutical preparation containing a steroid compound together with a vitamin D analogue. U.S. Pat. No. 5,565,462 relates to topical pharmaceutical compositions containing certain xanthine compounds, and where said compositions may additionally contain active compounds, such as steroids and vitamin D and its derivatives. However, there is no disclosure of a topical composition containing both a steroid and a vitamin D or vitamin D analogue or derivative, nor is there any description of a method of preparing such a composition.

The following example describes the difficulties encountered when the skilled person wishes to prepare a combination composition for topical use comprising both a vitamin D or a vitamin D analogue or derivative and a topical steroid: The vitamin D analogue calcipotriol, as well as other examples of vitamin D analogues, requires a pH value above 8 for maximum stability, whereas corticosteroids such as Betamethasone (9-fluoro-11,17,21-trihydroxy-16-methylpregna-1,4-diene-3,20-dione) require pH values in the range of 4–6 for maximum stability. Since the base auxiliary materials and additives traditionally used in preparing topical formulations, such as creams and/or ointments, involve having some kind of acid or alkaline nature or reaction ability, it has therefore hitherto not been possible to combine the two active compounds in one single formulation while maintaining good stability of the active compounds.

Consequently, physicians have had to resort to letting patients under this type of two-component regimen perform sequential application of two creams/ointments, each containing one of the compounds formulated at its maximum stability pH. This may lead to incompatibility of the preparations so that patients must, e.g., apply one cream/ointment in the morning and the other in the evening. Needless to say, patient compliance as well as correct administration dosage is a problem under such circumstances. Richards, H. L. et al. report in *J Am Acad Dermatol* 1999 October; 41(4):581–3 on a study of patients with psoriasis and their compliance with medication. They report that poor compliance with treatment advice in chronic conditions, such as psoriasis, represents a major challenge to health care professionals: Thirty-nine percent of participants reported that they did not comply with the treatment regimen recommended. The noncompliant group had a higher self-rated severity of psoriasis, were younger, and had a younger age at onset than those who were compliant. The noncompliant group reported that psoriasis had a greater impact on daily life.

It is therefore an object of the present invention to provide a pharmaceutical composition for dermal use where said composition alleviates the inconveniences of a two-component or multi-component regimen for the treatment of psoriasis and other inflammatory skin diseases including nail diseases. The provision of said composition will result in a substantial improvement in quality of life for a large population of psoriasis patients, especially the noncompliant group having a higher self-rated severity of psoriasis, being younger, and having a younger age at onset than those who are compliant.

SUMMARY OF THE INVENTION

In order to solve the above mentioned problems, the invention provides a pharmaceutical composition for dermal use, said composition comprising a first pharmacologically active component A consisting of at least one vitamin D or vitamin D analogue and a second pharmacologically active component B consisting of at least one corticosteroid.

DETAILED DESCRIPTION OF THE INVENTION

As a first pharmacologically active component A it is preferred to use a compound selected from the group consisting of seocalcitol; calcipotriol; calcitriol; tacalcitol, maxacalcitol; paricalcitol; falecalcitriol; $1\alpha$, 24S-dihydroxy-vitamin D2; and 1(S),3(R)-dihydroxy-20(R)-[((3-(2-hydroxy-2-propyl)-phenyl)-methoxy)-methyl]-9,10-seco-pregna-5(Z),7(E),10(19)-triene, as well as mixtures thereof.

More preferred are vitamin D analogues selected from the group consisting of calcipotriol, calcitriol, tacalcitol, maxacalcitol, and 1(S),3(R)-dihydroxy-20(R)-[((3(2-hydroxy-2-propyl)-phenyl)-methoxy)-methyl]-9,10-seco-pregna-5(Z),7(E),10(19)-triene as well as mixtures thereof. Synthetic vitamin D analogues are more preferred in the compositions according to the invention than naturally occurring vitamin D's or vitamin D derivatives, since the therapeutic effects of the latter may be less selective for the treatment of skin diseases, such as psoriasis.

Further non-limiting examples of vitamin D compounds constituting the first pharmacologically active component A are:

alphacalcidol;
$1\alpha$-hydroxy-vitamin D2;
$1\alpha$-hydroxy-vitamin D5;
1(S),3(R)-Dihydroxy-20(R)-(5-ethyl-5-hydroxy-1-heptyl)-9,10-secopregna-5(Z),7(E),10(19)-triene;
1(S),3(R)-Dihydroxy-20(R)-(6-hydroxy-6-methyl-1-heptyl)-9,10-secopregna-5(2),7(E)-10(19)-triene;
1(S),3(R)-Dihydroxy-20(R)-(6-hydroxy-6-methylhept-1(E)-ene-1-yl-9,10)-secopregna-5(Z),7(E),10(19)-triene;

1(S),3(R)-Dihydroxy-20(R)-(6-ethyl-6hydroxy-1-octyl)-9,10)-secopregna-5(Z),7(E),10(19)-triene;

1(S),3(R)-Dihydroxy-20(R)-(7-hydroxy-7-methyl-1-octyl)-9,10)-secopregna-5(2),7(E),10(19)-triene;

1(S),3(R)-Dihydroxy-20(R)-(7-hydroxy-7-methyloct-1(E)-en-1-yl-9,10)-secopregna-5(Z),7(E),10(19)-triene;

1(S),3(R)-Dihydroxy-20(R)-(6'-methyl-1'-heptyl)-9,10-secopregna-5(Z),7(E),10(19)-triene;

1(S),3(R)-Dihydroxy-20(S)-(5'-hydroxy-5'-methyl-1'-hexyloxy)-9,10-secopregna-5(Z),7(E),10(19)-triene;

1(S),3(R)-Dihydroxy-20(R)-(4'-hydroxy-4'ethyl-1'-hexyloxy)-9,10-seco-pregna-5(Z),7(E),10(19)-triene;

1(S),3(R)-Dihydroxy-20(R)-(6'-hydroxy-1'-hexyloxy-9,10-seco-pregna-5(Z),7(E),10(19 )-triene;

1(S),3(R)-Dihydroxy-20(R)-(5'-hydroxy-5'-ethyl-1'-heptyloxy)-9,10-seco-pregna-5(,7(E),10,19-triene;

1(S),3(R)-Dihydroxy-20(R)-(5'-hydroxy-5'-methyl-1'-hexyloxy)-9,10-seco-pregna-5(Z),7(E),10(19)-triene;

1(S),3(R)-Dihydroxy-20(R)-(5'-methyl-1'-hexyloxy)-9,10-seco-pregna-5(Z),7(E),$_{10}$(19)-triene;

1(S),3(R)-Dihydroxy-20(R)-(4'-hydroxy4'-(1"-propyl)-1'-heptyloxy)-9,10-seco-pregna-5(Z),7(E),10(19)-triene;

1(S),3(R)-Dihydroxy-20(R)-(4'-hydroxy-4'-methyl-1'-pentyloxy)-9,10-seco-pregna-5(Z),7(E),10(19)-triene;

1(S),3(R)-Dihydroxy-20(R)-(3'-hydroxy-3'-methyl-1'-butyloxy)-9,10-seco-pregna-5(Z),7(E),10(19)-triene;

1(S),3(R)-Dihydroxy-20(S)-(4-hydroxy-4-methyl-1-pentyl)-9,10-secopregna-(5Z),7(E),10(19)-triene;

1(S),3(R)-Dihydroxy-20(S)-(5-ethyl-5-hydroxy-1-hept-yl)-9,10-secopregna-5(Z),7(E),10(19)-triene;

1(S),3(R)-Dihydroxy-20(S)-(5-ethyl-5-hydroxy-hept-1(E)-en-1-yl),9,10-secopregna-5(2),7(E),10(19)-triene;

1(S),3(R)-Dihydroxy-20-(5'-hydroxy-1'-methyl-hexa-1'(E),3'(E)-dien-1'-yl)-9,10-secopregna-5(2),7(E),10(19)-triene;

1(S),3(R)-Dihydroxy-20-(5'-ethyl-5'hydroxy-hepta-1'(E),3'(E)-dien-1'-yl)-9,10-secopregna-5(Z),7(E),10(19)-triene;

1(S),3(R)-Dihydroxy-20-(6'-hydroxy-hexa-1'(E),3'(E)-dien-1'-yl)-9,10-secopregna-5(Z),7(E),10(19)-triene;

1(S),3(R)-Dihydroxy-20-(5'-cyclopropyl-5'-hydroxy-penta-1'(E),3'(E)-dien-1'-yl)-9,10-secopregna-5(Z)-7(E),10,19-triene (5'(R) and 5'(S) isomers);

1(S),3(R)-Dihydroxy-20-(6'-hydroxy-6'-methyl-hepta-1'(E),3"(E)-dien-1'-yl)-9,10-secopregna-5(Z),7(E),10(19)-triene;

1(S),3(R)-Dihydroxy-20(R)-(3-(2-hydroxy-2-pentyl)-phenylmethoxy)-9,10-seco-pregna-5(Z),7(E),10(19)-triene;

1(S),3(R)-Dihydroxy-20(R)-(3-(3hydroxy-3-propyl)-phenylmethoxy)-9,10-seco-pregna-5(Z),7(E),10(19)-triene;

1(S),3(R)-Dihydroxy-20(R)-(4-hydroxy-4-methyl-1-pentyloxymethyl)-9,10-seco-pregna-5(Z),7(E),10(19)-triene;

1(S),3(R)-Dihydroxy-20(R)-(4-hydroxy-4-methyl-1-pent-2-ynyloxymethyl)-9,10-seco-pregna-5(Z),7(E),10(19)-triene;

1(S),3(R)-Dihydroxy-20(R)-(4-hydroxy-4-trifluoromethyl-5,5,5-trifluoro-1-pent-2-ynyloxymethyl)-9,10-secopregna-5(Z),7(E),10(19)-triene;

1(S),3(R)-Dihydroxy-20(R)-[3-(2-hydroxy-2-propyl)-phenoxymethyl]-9,10seco-pregna-5(Z),7(E),10(19)-triene;

1(S),3(R)-Dihydroxy-20(R)-(3-hydroxy-3ethyl-1-pentylthiomethyl)-9,10-seco-pregna-5(Z),7(E),10(19)-triene;

1(S),3(R)-Dihydroxy-20(R)-(3-hydroxy-3-ethyl-1-pentylsulphonylmethyl)-9,10-seco-pregna-5(Z),7(E),10(19)-triene;

1(S),3(R)-Dihydroxy-20(R)-(3-((1-hydroxy-1-methyl)ethyl)phenylthiomethyl)-9,10-seco-pregna-5(Z),7(E),10(19)-triene;

1(S),3(R)-Dihydroxy-20(R)-(3,3-difluoro-4-hydroxy-4-methyl-1-pentyloxymethyl)-9,10-seco-pregna-5(Z)-7(E),10(19)-triene;

1(S),3(R)-Dihydroxy-20(R)-(6'-ethyl-6'-hydroxy-oct-1'-yn-1'-yl)-9,10-seco-pregna-5(Z),7(E)-10(19)-triene;

1(S),3(R)-Dihydroxy-20(R)-(7'-ethyl-7'-hydroxy-non-1'-yn-1'-yl)-9,10-seco-pregna-5(Z),7(E)-10(19)-triene;

1(S),3(R)-Dihydroxy-20(R)-(1,5-dihydroxy-5-ethyl-2-heptyn-1-yl)-9,10-seco-pregna-5(Z),7(E)-10(19)-triene; isomer A;

1(S),3(R)-Dihydroxy-20(R)-(5-ethyl-5-hydroxy-1-methoxy-2-heptyn-1-yl)-9,10-seco-pregna-5(Z),7(E)-10(19)-triene; isomer A;

1(S),3(R)-Dihydroxy-20(R)-(1-ethoxy-5-ethyl-5-hydroxy-2-heptyn-1-yl)-9,10-seco-pregna-5(Z),7(E)-10(19)-triene; isomer A;

1(S),3(R)-Dihydroxy-20(R)-(1-methoxy-4-hydroxy-4-ethyl-2-hexyn-1-yl)-9,10-seco-pregna-5(Z),7(E)-10(19)-triene; isomer A;

1(S),3(R)-Dihydroxy-20(R)-(1-ethoxy-4-hydroxy-4-ethyl-2-hexyn-1-yl)-9,10-seco-pregna-5(Z),7(E)-10(19)-triene; isomer A;

1(S),3(R)-Dihydroxy-20-(4-ethyl-4-hydroxy1-hexyn-1-yl)-9,10-seco-pregna-5(Z),7(E)-10(19)17(20)(Z)-tetraene;

1(S),3(R)-Dihydroxy-20-(5-ethyl-5-hydroxy-1-heptyn-1-yl)-9,10-seco-pregna-5(Z),7(E)-10(19),17(20)(Z)-tetraene;

1(S),3(R)-Dihydroxy-20-(6-ethyl-6-hydroxy-1-octyn-1-yl)-9,10-seco-pregna-5(Z),7(E)-10(19),17(20)(Z)-tetraene;

1(S),3(R)-Dihydroxy-20(R)-(5-ethyl-4,4-difluoro-5-hydroxy-heptyloxy)-9,10-seco-pregna-5(Z),7(E),10(19)-triene;

1(S)3(R)-Dihydroxy-20(R)-(4,4-dichloro-5-hydroxy-5-methyl-hexyloxy)-9,10-seco-pregna-5(Z),7(E)-10(19)-triene;

1(S),3(R)-Dihydroxy-20(R)-(4,4-difluoro-5-hydroxy-5-methyl-hexyloxy)-9,10-seco-pregna-5(Z),7(E)-10(19)-triene;

1(S),3(R)-Dihydroxy-20(R)-(4-fluoro-4-methyl-pentyloxy)-9,10-seco-pregna-5(Z),7(E),10(19)-triene;

1(S),3(R)-Dihydroxy-20(R)-(4-ethyl-4-fluoro-hexyloxy)-9,10-seco-pregna-5(Z),7(E),10(19)-triene;

1(S),3(R)-Dihydroxy-20(R)-(5-fluoro-5methyl-hexyloxy)-9,10-seco-pregna-5(Z),7(E),10(19)-triene;

1(S),3(R),20(S)-Trihydroxy-20-(4-ethyl-4-hydroxy-1-hexyl)-9,10-secopregna-5(Z),7(E),10(19)-triene;

1(S),3(R)-Dihydroxy-20(S)-methoxy-20-(4-ethyl-4-hydroxy-1-hexyl)-9,10-secopregna-5(Z),7(E),10(19)-triene;

1(S),3(R)-Dihydroxy-20(S)-ethoxy-20-(4-ethyl-4-hydroxy-1-hexyl)-9,10-secopregna-5(Z),7(E),10(19)-triene;

1 (S),3(R)-Dihydroxy-20(S)-[3-(2-hydroxy-2-methyl-1-propoxy)-prop-1E-en-1-yl]-9,10-seco-pregna-5(Z),7 (E),10(19)-triene;

1(S),3(R)-Dihydroxy-20(R)-(4-ethyl-4-hydroxy-1-hexylthio)-9,10-seco-pregna-5(Z),7(E),10(19)-triene;

1(S),3(R)-Dihydroxy-20(R)-[5-methyl-5-hydroxy-1-hexylthio]-9,10-seco-pregna-5(Z),7(E),10(19)-triene;

1(S),3(R)-Dihydroxy-20(R)-[3-(1-methyl-1-hydroxyethyl)benzylthio]-9,10-seco-pregna-5(Z),7E), 10(19)-triene;

1(S),3(R)-Dihydroxy-20(R)-(3-methyl-3-hydroxy-1 butylthio)-9,10-seco-pregna-5(Z)-7(E),10(19)-triene;

1(S),3(R)-Dihydroxy-20(R)-(5-ethyl-5-hydroxy-hept-1 (E)-en-3-yn-1-yl)-9,10-seco-pregna-5(Z),7(E),10(19)-triene;

24-oxo-1(S),3(R),25-Trihydroxy-20(S)-9,10-seco-cholesta-5(Z),7(E),10,19-triene;

1(S),3(R) -Dihydroxy-20(R)-(3-oxo-4-hydroxy-4-ethyl-1-hexyloxy)-9,10-seco-pregna-5(Z),7(E),10(19)-triene;

1(S),3(R)-Dihydroxy-20-methyl-18-(5-methyl-5-hydroxy-hexyloxy)-9,10-seco-pregna-5(Z),7(E),10 (19)-triene;

1(S),3(R)-Dihydroxy-20-methyl-18-(4-ethyl-4-hydroxy-hexyloxy)-9,10-seco-pregna-5(Z),7(E),10(19)-triene;

1(S),3(R)-Dihydroxy-20-methyl-18-(4-ethyl-4-hydroxy-hex-2-ynyloxy)-9,10-seco-pregna-5(Z),7(E),10(19)-triene;

1(S),3(R)-Dihydroxy-20-methyl-18-(4-hydroxy-4-methylpentyloxy)-9,10-seco-pregna-5(Z),7(E),10(19)-triene;

1(S),3(R)-Dihydroxy-20-methyl-18-(4-hydroxy-4-methylpent)-2-yn-1-yloxy)-9,10-seco-pregna-5(Z),7 (E),10(19)-triene;

1(S)3(R)-Dihydroxy-20-methyl-18-(3,1-hydroxy-1-methylethyl)phenylmethyloxy)-9,10-seco-pregna-5 (Z),7(E),10(19)-triene;

1(S),3(R)-Dihydroxy-20(R)-(1-methoxy-4-hydroxy-4-methyl-1-pentyl)-9,10-seco-pregna-5(Z),7(E),10(19)-triene; isomer A;

1(S),3(R)-Dihydroxy-20(R)-(1-ethoxy4-hydroxy-4-methyl-1-pentyl) -9,10-seco-pregna-5(Z),7(E),10(19)-triene; isomer A;

1(S),3(R),25-Trihydroxy-(20(S)-9,10-seco-cholesta-5(Z), 7(E),10(19),23(E)-tetraene;

1(S),3(R)-Dihydroxy-(20(S)-(6'-hydroxy-6'-methyl-4' (E)-hepten-1'yl)-9,10-seco-pregna-5(Z),7(E),10(19)-triene;

1(S),3(R),22(S),25-Tetrahydroxy-20(R),9,10-seco-cholesta-5(Z),7(E),10(19),23(E)-tetraene;

22(S)-Ethoxy-1(S)-3(R),25-trihydroxy-10(R)-,9,10-seco-cholesta-5(Z),7(E),10(1,23(E),-tetraene;

1(S),3(R)-Dihydroxy-20(S)-(3-(1-hydroxy-1-methylethyl)phenoxymethyl)-9,10-secopregna-5(Z),7 (E),10(19),16-tetraene or the corresponding 20(R) isomer;

1(S),3(R)-Dihydroxy-20(S)-(3(1-hydroxy-1-methylethyl) phenylthiomethyl)-9,10-secopregna-5(Z),7(E),10(19), 16-tetraene or the corresponding 20(R) isomer;

1(S),3(R)-Dihydroxy-20(S)-(4-hydroxy-4-methylpent-1-yl)-9,10-secopregna-5(Z),7(E),10(19), 16-tetraene;

1(S),3(R)-Dihydroxy-20(R)-(5-ethyl-5-hydroxyhept-1-yl)-9,10-secopregna-5(Z),7(E),10(19),16-tetraene or the corresponding 20(S) isomer;

1(S),3(R)-Dihydroxy-20(R)-(5-ethyl-5-hydroxyhepta-1 (E),3(E)-dien-1-yl)-9,10-secopregna-5(Z),7(E),10(19), 16-tetraene or the corresponding 20(S) isomer;

1(S),3(R)-Dihydroxy-20(R)-(3cyclopropyl-3-hydroxyprop-1(E)-en-1-yl)-9,10-secopregna-5(Z),7 (E),10(19),16-tetraene (24(S) isomer) or the corresponding 24(R) isomer; and 1(S),3(R)-Dihydroxy-20(1,5-dihydroxy-5-ethyl-2-heptyn-1-yl)-9,10-secopregna-5(Z),7(E),10(19),17(20) Z-tetraene, both 22-isomers.

As a second pharmacologically active component B it is preferred to use a group I, II or III topical steroid, more preferably a medium to weak acting steroid (groups I and II). Component B is preferably selected from the group consisting of Betamethasone (9-fluoro-11,17,21-trihydroxy-16-methylpregna-1,4-diene-3,20-dione) and esters thereof such as the 21-acetate, 17-adamantoate; 17-benzoate, 17-valerate, and 17,21-dipropionate; Alclomethasone and esters thereof such as the dipropionate; Clobetasole and esters thereof such as the propionate; Clobetasone and esters thereof such as the 17-butyrate; Desoximetasone; Diflucortolon and esters thereof, Diflorasone and esters thereof such as the diacetate; Fluocinonid; Flumetasone and esters thereof such as the pivalate; Fluocinolon and ethers and esters thereof such as the acetonide; Fluticasone and esters thereof such as the propionate; Fluprednidene and esters thereof such as the acetate; Halcinonide; Hydrocortisone and esters thereof such as the -17-butyrate; Mometasone and esters thereof such as the furoate; and Triamcinolon and ethers and esters thereof such as the acetonide; as well as mixtures thereof. More preferred examples of the corticosteroids are Betamethasone or esters thereof such as the 17-valerate or the 17,21-dipropionate, Clobetasole or esters thereof such as the propionate, Triamcinolon or ethers and/or thereof such as the acetonide or the acetonide-21-N-benzoyl-2-methyl-β-alaninate or the acetonide-21-(3,3-dimethylbutyrate), or Hydrocortisone or esters thereof such as the 17-butyrate.

Moreover, the invention relates to a pharmaceutical compositions for dermal use which contain at least one vitamin D or vitamin D analogue and at least one corticosteroid and which exhibits a higher efficacy in the treatment of psoriasis and other inflammatory skin diseases in humans and other mammals than any of the pharmacologically active components used alone. Said efficacy is preferably measured as percentage change in PASI score in psoriasis and related skin diseases, such as sebo-psoriasis and seborrhoic dermatitis.

PASI (Psoriasis Area and Severity Index) score assesses the extent and severity of the patient's psoriasis. The following formulae are used to calculate the PASI score:

Arms $0.2(R+T+S)E=X$

Trunk $0.3(R+T+S)E=Y$

Legs $0.4(R+T+S)E=Z$

Where R=score for redness, T=score for thickness, S=score for scaliness, and E=score for extent where the score is assessed according to a scale from 0 to 4 as follows: 0=no involvement, 1=<10%, 2=10–29&, 3=30–49%, and 4=50–69%. The sum of X+Y+Z gives the total PASI score which can range from 0 to 64.8.

DESCRIPTION OF THE DRAWINGS

FIG. 1 shows an efficacy of the preparation of the invention which by far exceeds the efficacy obtainable by the two single component preparations. The change in PASI score reflects in the group of patients treated with the preparation of the invention a success of treatment of psoriasis Fail hitherto unattainable by treatment with commercial preparations containing either calcipotriol or betamethasone, or by alternating treatment with such commercial preparations (cf. ) thus proving the advantage of having the two active components present in the same preparation. (EOT=end of treatment).

FIG. 2 is a table showing the figures for percentage change in PASI score at each visit and end of treatment for the same clinical trial as described for FIG. 1.

FIG. 4 is a table showing the figures for percentage of responders as a result of investigators' assessment of overall efficacy at each visit and end of treatment, cf. FIG. 3, in the same clinical trial as for FIG. 1.

TOPICAL FORMULATIONS

Figure 1:
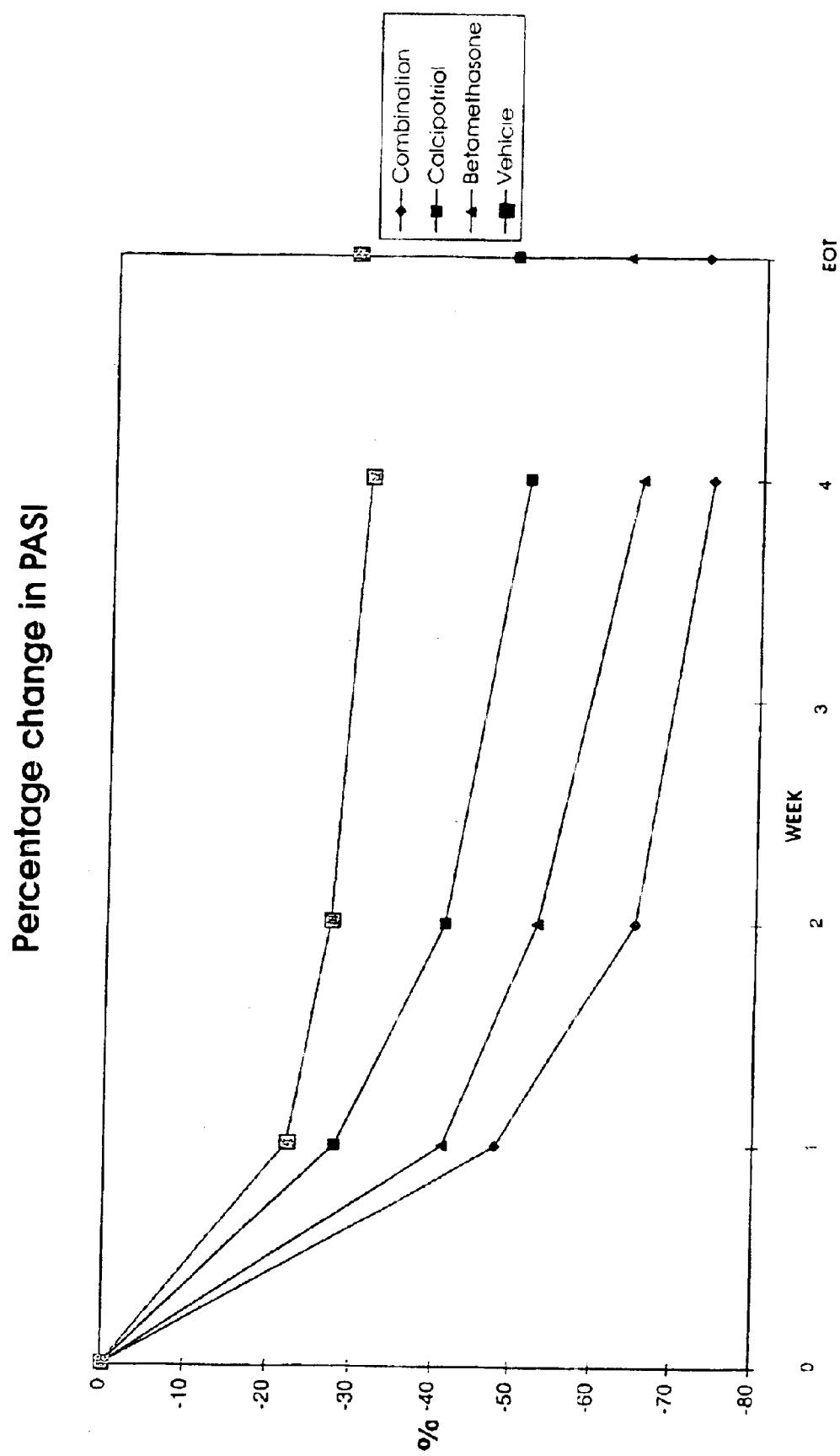
FIG. 1 is a graphic illustration of the percentage change in PASI score obtained during 4 weeks of clinical trial where the efficacy of a preparation according to the invention containing calcipotriol hydrate (52.2 µg/g) and betamethasone dipropionate (0.643 mg/g) is compared to that of a preparation in the same vehicle containing only calcipotriol hydrate (52.2 µg/g) and a preparation in the same vehicle of betamethasone dipropionate (0.643 mg/g).
Figure 3:
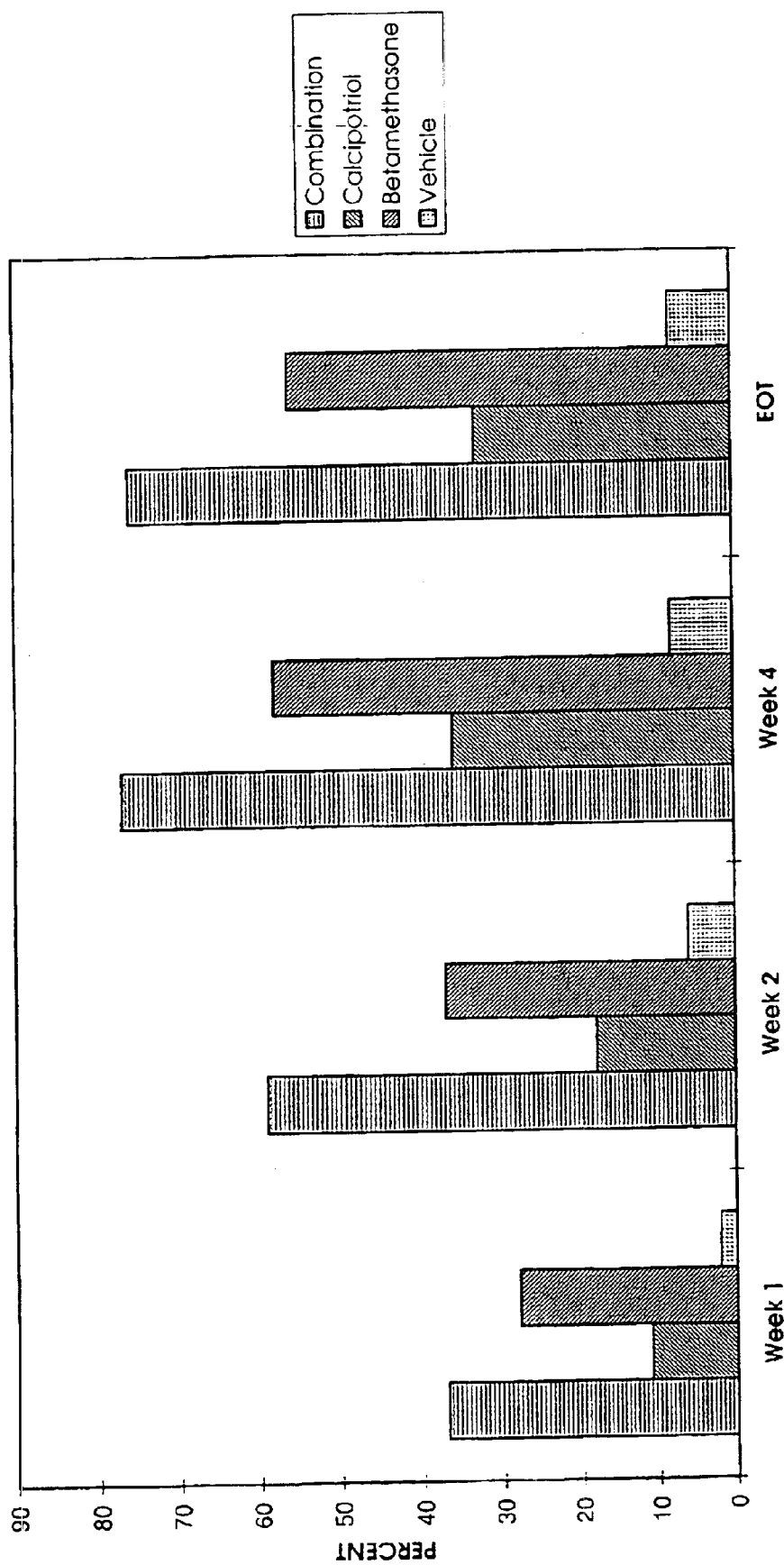
FIG. 3 is a bar diagram showing percentage of responders as a result of investigators' assessment of overall efficacy at each visit and end of treatment in the same clinical trial as for FIG. 1. Responders are defined as patients with marked improvement or clearance.

In a preferred embodiment the invention provides a topical pharmaceutical composition in the form of an ointment, a cream, a lotion, preferably a scalp lotion, a liniment or other spreadable liquid or semi liquid preparation which is, preferably, non-aqueous or in the form of an oil-in-water or water-in-oil emulsion. In one preferred embodiment, the composition of the invention is a monophase composition, i.e. a composition comprising a single solvent system, such as an ointment.

In a further preferred embodiment the invention provides a non-aqueous pharmaceutical composition for dermal use, said composition comprising
- a first pharmacologically active component A consisting of at least one vitamin D analogue;
- a second pharmacologically active component B consisting of at least one corticosteroid;
- the difference between the optimum stability pH of a first pharmacologically active component A and the optimum stability pH of a second pharmacologically active component B being at least 1; and
- at least one solvent component C selected from the group consisting of:
  - (i) compounds of the general formula $R^3(OCH_2C(R^1)H)_xOR^2$ (I) wherein x is in the range of 2–60, $R^1$ in each of the x units independently is H or $CH_3$, $R^2$ is straight chain or branched $C_{1-20}$alkyl or benzoyl, and $R^3$ is H or phenylcarbonyloxy;
  - (ii) di-(straight or branched)-$C_{4-10}$alkyl esters of $C_4$–$C_8$dicarboxylic acids;
  - (iii) straight or branched $C_{12-18}$-alkyl benzoates;
  - (iv) straight or branched $C_{2-4}$-alkyl esters of straight or branched $C_{10-18}$-alkanoic or -alkenoic acids;
  - (v) propyleneglycol diesters with $C_{8-14}$-alkanoic acids; and
  - (vi) branched primary $C_{18-24}$alkanols, and wherein components A and B are as defined above.

It has been found that in such combination compositions containing a solvent component C, the active components can co-exist without degradation, despite their different pH/stability profiles. The tendencies of the active compounds to affect one another with regard to pH is minimised or eliminated.

It is preferred that the maximum difference in optimum stability pH between the pharmacologically active compounds is at least 1.5, more preferred at least 2, in particular at least 2.5, more particularly at least 3, especially at least 4, such as at least 5.

In the general formula (I) defined above, it is preferred that the factor x (which designates the number of the units within the parentheses) is in the range 4–50, more preferably 4–40, in particular 4–30, especially 5–25, more especially 10–20, such as about 15. It is further preferred that $R^{1-}$ is $CH_3$.

It is preferred that said component C is selected from compounds of the general formula $H(OCH_2C(R^1)H)_xOR^2$ (II) where $R^1$, x, and $R^2$ are as defined above, and mixtures thereof.

As nor-limiting specific examples of the types (i)–(vi) of the solvent component C defined above may be mentioned the following, including trade names:

Arlamol E (polyoxyethylene(15) stearyl ether);

Arlamol DoA (diisooctyl ester of adipic acid);

Arlasolve 200 (Polyoxyethylene-20-isohexadecyl ether);

Eutanol G (2-octyldodecanol);

Finsolv (Isostearyl benzoate);

Finsolv P (polyoxypropylene-15-stearyl ether benzoate);

Isopropylesters of straight or branched $C_{10}$–$C_{18}$alkanoic or alkenoic acids such as isopropyl myristate, isopropyl palmitate, isopropyl isostearate, isopropyl linolate and isopropyl monooleate;

Miglyol 840 (Propylene glycol diester of caprylic and caprinic acid);

DPPG (propylene glycol dipelagonate);

Procetyl AWS $(CH_3(CH_2)_{14}CH_2(OCH(CH_3)CH_2)_5—(OCH_2)_{20}OH)$.

The compositions of the present invention may be prepared in accordance with methods well known to the person skilled in the field of pharmacy. Thus, the non-aqueous compositions may be prepared by incorporating the components into a well known ointment or lotion base excipient such as white soft paraffin (also known as vaseline) or Plastibase™ (a base prepared from polyethylene (average MW about 21,000) and paraffin liquid) or ESMA-P™ (a microcrystalline wax). As an example, preparation of a composition according to the invention is typically performed by melting while soft paraffin, adding a solution (typically at a concentration in the range of 0.0005–2.5% w/w) of the vitamin D analog in the required amount of solvent component C, e.g. Arlamol E, followed by addition of a dispersion of the corticosteroid component B in paraffin oil, typically with a particle size of from 0.1 to 20 µm, and then cooling the mixture. Typical content ranges of the various components in the finished composition according to the invention are 0.005 to 0.1% w/w of the corticosteroid component B, from 0.0001 to 0.025% w/w of the vitamin D analog component A, and from 1 to 20% w/w of the solvent component C, the remainder typically being primarily base excipient such as the abovementioned white soft paraffin and/or paraffin oil. The composition may also contain other commonly used additives such as antioxidants (e.g. α-tocopherol).

The composition according to the invention provides the following therapeutic advantages in the treatment of skin diseases, such as psoriasis, sebo-psoriasis and related disorders, compared to the single compound therapy or combination therapy of the prior art:

A clinical investigation has showed that treatment of psoriasis patients with a composition according to the invention comprising calcipotriol and betamethasone resulted in a faster onset of healing and a more effective healing of plaques than patients treated with only one of the active compounds.

A composition combining a vitamin D analogue and a topical steroid provides synergy in the form of additional benefit to the patient apart from the direct therapeutic value of the active substances. It has been shown that the skin irritative side effects of a vitamin D analogue, such as calcipotriol, is alleviated by the simultaneous application of a steroid, such as betamethasone, onto psoriatic skin, an effect that is only attainable using a two-component or multi-component treatment regimen where a vitamin D analogue and a steroid cannot be applied simultaneously to affected skin due to incompatibility of the praparations. When both a vitamin D analogue and a topical steroid are used in a combination treatment of psoriasis it has hitherto been necessary to use separate applications, typically one in the morning and the other in the evening, making it impossible to obtain any synergistic effect of the two types of active compounds (cf. Ortonne, J. P., Nouv. Dermatol., 1994, 13(10), p. 746–751), or where a certain degree of synergistic effect, such as less skin irritation, has been reported for a two-component regiment (cf. Kragballe, K. et al. *Br J Dermatol* 1998 Oct;139(4):649–54, and Ruzicka, T. et Lorenz, B. *Br J Dermatol* 1998, 138(2), 254–58) a substantial proportion of psoriasis patients will not benefit due to non-compliance with the treatment regimen.

Satisfactory medical treatment of skin disorders, such as psoriasis, can be attained in a shorter period of time using the composition according to the invention resulting in a reduction of steroid side effects, such as skin atrophy and rebound. Besides, it can be anticipated that even a milder acting steroid of group 1, such as hydrocortisone which is presently not administered for psoriasis treatment, will be efficient in reducing or even eliminating the skin irritation which often follows calcipotriol treatment.

Thus, the tolerance of the treatment will be considerably improved due to reduction of side effects of the active compounds.

Instructions for treatment will be simpler when a single preparation is needed resulting in improved compliance for the patient and the possibility of efficient treatment of a much larger population of psoriasis patients.

Instructions for treatment will be simpler when a single preparation is needed resulting in improved safety for the patient.

The invention also relates to a preferred pharmaceutical preparation according to the invention which is especially useful for the treatment of psoriatic skin diseases which are complicated by additional fungal infections, and which further contains an anti-fungal agent selected, e.g., from the group consisting of miconazol, clotrimazol, terbinafin, ciclopirox, bifonazol, nystatin, ketoconazol, econazol, and amorolfine.

Preferably, the compositions according to the invention do not contain other therapeutically effective compounds selected from the group consisting of the xanthine derivatives pentoxifylline, propentofyllin, and torbafylline, or any other xanthine or xanthine derivative.

The invention also relates to a method of treatment of psoriasis and related skin diseases comprising topically administering an effective amount of a composition according to the invention to a patient in need of such treatment. Said method preferably comprises topical administration once or twice daily of a medically sufficient dosage of said composition.

The composition according to the invention preferably contains 0.001–5 mg/g or ml or more preferably 0.01–0.25 mg/g or ml of said component A and 0.05–0.1 mg/g or ml of said component B.

The invention is further illustrated by the following, non-limiting examples.

EXAMPLE 1

Ointment Containing Calcipotriol and Betamethasone Dipropionate 919.3 g of White Soft Paraffin is melted at 80° C. followed by cooling to 70° C. and maintaining that temperature. Thereafter, 52.2 mg Calcipotriol hydrate (50 mg Calcipotriol) is dissolved in 50 g Arlamol E (polyoxypropylene-15-stearyl ether) to form a solution (Solution 1). Solution 1 is then added slowly into the molten paraffin while stirring.

Betamethasone (0.5 g, in the form of 0.643 g of its dipropionate) in particulate form (99%<15 μm) is dispersed in 30 g Paraffin Liquid to form Dispersion 1. Dispersion 1as well as 20 mg α-tocopherol are added to the Calcipotriol-containing paraffin mixture of while stirring, after which the mixture is cooled to below 30° C. to give a composition according to the invention with the following composition:

| 1 g of ointment contains: | Betamethasone | 0.5 mg |
|---|---|---|
| | (as dipropionate 0.643 mg) | |
| | Calcipotriol | 50 μg |
| | (as hydrate 52.2 μg) | |
| | Paraffin, Liquid | 30 mg |
| | Polyoxypropylene-15-Stearyl Ether | 50 mg |
| | α-Tocopherol | 20 μg |
| | White Soft Paraffin to make | 1 g |

EXAMPLE 2

Stability Test

The chemical stability of the two active components was tested after storage for 1 month at 40° C. and 3 months at 25° C. and 40° C., respectively. The quantitative content of Calcipotriol was determined by HPLC.

The Calcipotriol was extracted from the preparation into a mixture of methanol and 0.01M diammonium hydrogen-phosphate (70:30) and quantified under the following HPLC conditions: Column: about 125 mm ø 4 mm (i.d.) stainless steel column with LiChrospher RP-18, 5 μm; mobile phase: acetonitrile-methanol-0.01 M aqueous ammonium phosphate pH 6 (20:50:30); flow: about 2 ml/min; detection: variable wavelength UV-detector set at 265 nm. Calcipotriol and the related substances were separated by the reverse phase HLPC-method described above; Column: Superspher RP-18, 4 μm; Flow: 1.2 ml/min. The quantitative content of Betamethasone Dipropionate was determined by HLPC.

The Betamethasone Dipropionate was extracted from the preparation into a mixture of acetonitrile:water (50:55) and quantified under the following HPLC conditions: Column: About 125 mm ø 4 mm (i.d.) stainless steel column packed with LiChrospher RP-18, 5 μm. Mobile phase: Acetonitrile:water (50:55). Flow: 2 ml/min. Detection: Variable wavelength UV-detector set at 240 nm. The related substances besides betamethasone were determined by a reverse phase HLPC-method analogous to the above. Betamethasone: Determined as above with the exception of the mobile phase: Acetonitrile/methanol/0.05M buffer pH7 (25:5:70).

The results are shown in the following Table 1.

TABLE 1

|  | Calcipotriol μg/g | Calcipotriol-related substances % | Betamethasone dipropionate mg/g | Betamethasone-related substances % |
|---|---|---|---|---|
| Start 25° C. | 50.0 | 1.6 | 0.63 | 1.2 |
| 3 months 40° C. | 50.5 | 1.4 | 0.64 | 0.2 |
| 1 month | 48.0 | 2.1 | 0.64 | 0.6 |
| 3 months | 49.7 | 1.8 | 0.64 | 0.2 |

It will be seen from Table 1 that both Calcipotriol and Betamethasone ester are very stable under the test conditions.

The stability of Calcipotriol was compared to an similar ointment where propylene glycol was used as the solvent and lanolin used as an emulsifier. The composition of the comparison ointment was the same as the above with respect to Calcipotriol and Betamethasone dipropionate, as well as 10% w/w propylene glycol, 10% w/w anhydrous lanolin and 80% w/w White Soft Paraffin. The comparison ointment was stored for 2.5 months at 5° C. and 40° C., respectively. Only the content of Calcipotriol-related substances was determined in the manner described above. The results are shown in Table 2.

TABLE 2

| Calcipotriol related substances % | |
|---|---|
| 5° C. | 20 |
| 40° C. | 96 |

As it will be seen from the results, Calcipotriol is degraded almost completely in the comparison composition under the test conditions as opposed to a composition of the invention, where the Calcipotriol is retained with essentially no degradation.

EXAMPLE 3

Medical Skin Lotion Comprising a Two Phase Solvent System 1 g contains:

| | |
|---|---|
| Betamethasone (As Dipropionate 0.643 mg) | 0.5 mg |
| Calcipotriol (as Hydrate 52.2 μg) | 50 μg |
| Disodium Phosphate Dihydrate | 2.5 mg |

-continued

| | |
|---|---|
| Diazolidinyl Urea | 3 mg |
| Polyoxypropylene-15-Stearyl Ether (Arlamol ® E) | 50 mg |
| Isohexadecan (Arlamol ® HD) | 200 mg |
| Polyoxyethylene-2-Stearyl Ether (Brij ® 72) | 30 mg |
| Water, purified to make | 1 g |

Procedure for the preparation of 1 kg of lotion:

2.5 g Disodium Phosphate and 3 g Diazolidinyl Urea are dissolved in about 714 g water. The solution is heated to 60–70° C. to obtain the water phase. 30 g Polyoxyethylene-2-Stearyl Ether is melted together with 200 g Isohexadecan at 60–70° C. and a solution of 52.2 mg Calcipotriol Hydrate in 50 g Polyoxypropylene-15-Stearyl Ether is added to obtain the oil phase. The two phases are mixed during homogenisation, 643 mg Betamethasone Dipropionate is dispersed into the mixture, and the lotion is cooled during mixing to room temperature. The preparation is stable at 25° C. for >14 days.

What is claimed is:

1. A pharmaceutical composition for dermal use, said composition comprising:

a first pharmacologically active component A consisting of at least one vitamin D or vitamin D analogue selected from the group consisting of seocalcitol, calcipotriol, calcitriol, tacalcitol, maxacalcitol, paricalcitol, falecalcitriol, 1α,24S-dihydroxy-vitamin D2, 1(S),3(R)-dihydroxy-20(R)-[((3-(2-hydroxy-2-propyl)-phenyl)-methoxy)-methyl]-9,10-seco-pregna-5(Z),7(E),10(19)-triene and mixtures thereof; and a second pharmacologically active component B consisting of at least one corticosteroid, wherein the difference between the maximum stability pH of said first component A and the maximum stability pH of said second component B is at least 1; and at least one solvent component C selected from the group consisting of:
(i) compounds of the general formula $R^3(OCH_2C(R^1)H)_xOR^2$ (I) wherein x is in the range of 2–60, $R^1$ in each of the x units independently is H or $CH_3$, $R^2$ is straight chain or branched $C_{1-20}$alkyl or benzoyl, and $R^3$ is H or phenylcarbonyloxy;
(ii) di-(straight or branched)-$C_{4-10}$alkyl esters of $C_4$–$C_8$ dicarboxylic acids;
(iii) straight or branched $C_{12-18}$-alkyl benzoates;
(iv) straight or branched $C_{2-4}$-alkyl esters of straight or branched $C_{10-18}$-alkanoic or -alkenoic acids;
(v) propylenglycol diesters with $C_{8-14}$-alkanoic acids; and
(vi) branched primary $C_{18-24}$ alkanols.

2. The composition according to claim 1, wherein said vitamin D analogue is selected from the group consisting of calcipotriol, calcitriol, tacalcitol, maxacalcitol, 1(S),3(R)-dihydroxy-20(R)-[((3-(2-hydroxy-2-propyl)-phenyl)-methoxy)-methyl]-9,10-seco-pregna-5(Z),7(E),10(19)-triene, and mixtures thereof.

3. The composition according to claim 1 or 2, wherein the vitamin D analogue is effective against psoriasis and related disorders of the skin in humans and other mammals.

4. The composition according to claim 3, wherein said vitamin D analogue is calcipotriol or its hydrate thereof.

5. The composition according to claim 1 or 2, wherein said corticosteroid is selected from the group consisting of Betamethasone, Clobetasol, Clobetasone, Desoximethasone, Diflucortolon, Diflorasone, Fluocinonid, Flumethasone, Fluocinolon, Fluticasone, Fluprednidene, Halcinonide, Hydrocortisone, Mometason, Triamcinolon, and pharmaceutically acceptable esters and acetonides as well as mixtures thereof.

6. The composition according to claim 5, wherein said esters or acetonides are selected from the group consisting of 17-valerate, 17-propionate, 17,21-dipropionate, acetonide, acetonide-21-N-benzoyl-2-methyl-β-alaninate, acetonide-21-(3,3-dimethylbutyrate) and 17-butyrate.

7. The composition according to claim 1 or 2, wherein said corticosteroid is selected from the group consisting of group I topical steroid, group II topical steroid and group III topical steroid.

8. The composition according to claim 1 or 2, wherein said composition is in the form of a non-aqueous composition.

9. The composition according to claim 1 or 2, wherein said composition is in the form of a non-aqueous composition.

10. The composition according to claim 9, wherein said composition is an ointment.

11. The composition according to claim 10, wherein said composition has the following composition:

| | |
|---|---|
| Betamethasone | 0.5 mg |
| Calcipotriol | 50 μg |
| Paraffin, Liquid | 30 mg |
| Polyoxypropylene-15-Stearyl Ether | 50 mg |
| α-Tocopherol | 20 μg |
| White Soft Paraffin to make | 1 g. |

12. A lotion comprising the composition according to claim 1 or 2.

13. The composition according to claim 12, said composition having the following composition:

| | |
|---|---|
| Betamethasone | 0.5 mg |
| Calcipotriol (as Hydrate 52.2 μg) | 50 μg |
| Disodium Phosphate Dihydrate | 2.5 mg |
| Diazolidinyl Urea | 3 mg |
| Polyoxypropylene-15-Stearyl Ether | 50 mg |
| Isohexadecan | 200 mg |
| Polyoxyethylene-2-Stearyl Ether | 30 mg |
| Water, purified to make | 1 g. |

14. The composition according to claim 1, wherein said component C is selected from the group consisting of a compound of the general formula $H(OCH_2C(R^1)H)_xOR^2$ (II) and mixtures thereof, wherein where $R^1$, x, and $R^2$ are as defined in claim 1.

15. The composition according to claim 14, wherein where $R^1$ in the general formula is $CH_3$.

16. The composition according to claim 14, wherein said component C is polyoxypropylene-15-stearyl ether.

17. The composition according to claim 1 or containing 0.001–0.25 mg/g or ml of said component A and 0.005–0.1% w/w of said component B.

18. A method of treating psoriasis, sebopsoriasis or seborrhoic dermatitis, the method comprising topically administering an effective amount of the composition of claim 1 or 2, to a patient in need of such treatment.

19. The method of claim 18 comprising topical administration once or twice daily of a medically sufficient dosage of said composition.

20. The method of claim 18, wherein application of the composition results in a higher efficacy in the treatment of psoriasis, sebopsoriasis or seborrhoic dermatitis than the efficacy attainable when using any composition comprising said components A or B alone.

21. The method of claim 18, wherein the efficacy of said treatment is measured, and said efficacy is measured as a percentage change in Psoriasis Area and Severity Index score.

22. A pharmaceutical composition comprising:

a first pharmacologically active component A consisting of at least one vitamin D or vitamin D analogue selected from the group consisting of seocalcitol, calcipotriol, calcitriol, tacalcitol, maxacalcitol, paricalcitol, falecalcitriol, 1α,24S-dihydroxy-vitamin D2, 1(S),3(R)-dihydroxy-20(R)-[((3-(2-hydroxy-2-propyl)-phenyl)-methoxy)-methyl]-9,10-seco-pregna-5(Z),7(E),10(19)-triene and mixtures thereof; and a second pharmacologically active component B consisting of at least one corticosteroid, wherein the difference between the maximum stability pH of said first component A and the maximum stability pH of said second component B is at least 1; and at least one solvent component C selected from the group consisting of:

(i) compounds of the general formula $R^3(OCH_2C(R^1)H)_xOR^2$ (I) wherein x is in the range of 2–60, $R^1$ in each of the x units independently is H or $CH_3$, $R^2$ is straight chain or branched $C_{1-20}$alkyl or benzoyl, and $R^3$ is H or phenylcarbonyloxy;

(ii) straight or branched $C_{2-4}$-alkyl esters of straight or branched $C_{10-18}$-alkanoic or -alkenoic acids;

(iii) propylenglycol diesters with $C_{8-14}$-alkanoic acids; and (iv) branched primary $C_{18-24}$ alkanols;

wherein said pharmaceutical composition is storage stable, non-aqueous and in a single container.

23. The pharmaceutical composition of claim 22, wherein said pharmaceutical composition is stable when stored at 40° C. for 3 months.

* * * * *

UNITED STATES PATENT AND TRADEMARK OFFICE
CERTIFICATE OF CORRECTION

| | |
|---|---|
| PATENT NO. | : 6,753,013 C1 |
| APPLICATION NO. | : 95/000153 |
| DATED | : January 21, 2014 |
| INVENTOR(S) | : Erik Didriksen et al. |

Page 1 of 1

It is certified that error appears in the above-identified patent and that said Letters Patent is hereby corrected as shown below:

<u>In the Claims</u>:

Claim 51, Column 6, line 8, please change the dependency from claim "48" to claim --46--.

Signed and Sealed this
First Day of April, 2014

Michelle K. Lee
*Deputy Director of the United States Patent and Trademark Office*

/

(12) INTER PARTES REEXAMINATION CERTIFICATE (805th)
United States Patent
Didriksen et al.

(10) Number: US 6,753,013 C1
(45) Certificate Issued: Jan. 21, 2014

(54) PHARMACEUTICAL COMPOSITION

(75) Inventors: Erik Didriksen, Ballerup (DK); Gert Høy, Ballerup (DK)

(73) Assignee: Leo Pharmaceutical Products Ltd. A/S, Ballerup (DK)

Reexamination Request:
No. 95/000,153, Jul. 17, 2006

Reexamination Certificate for:
Patent No.: 6,753,013
Issued: Jun. 22, 2004
Appl. No.: 09/959,367
Filed: Oct. 22, 2001

(21) Appl. No.: 95/000,153

(22) PCT Filed: Jan. 27, 2000

(86) PCT No.: PCT/DK00/00033
§ 371 (c)(1),
(2), (4) Date: Oct. 22, 2001

(87) PCT Pub. No.: WO00/64450
PCT Pub. Date: Nov. 2, 2000

(30) Foreign Application Priority Data

Apr. 23, 1999 (DK) .................................. 1999 00561

(51) Int. Cl.
| | | |
|---|---|---|
| *A61K 9/06* | (2006.01) | |
| *A61K 9/10* | (2006.01) | |
| *A61K 9/14* | (2006.01) | |
| *A61K 31/41* | (2006.01) | |
| *A61K 31/573* | (2006.01) | |
| *A61K 31/58* | (2006.01) | |
| *A61K 31/59* | (2006.01) | |
| *A61K 31/593* | (2006.01) | |
| *A61K 47/10* | (2006.01) | |
| *A61K 47/14* | (2006.01) | |
| *A61K 47/32* | (2006.01) | |
| *A61P 17/06* | (2006.01) | |
| *A61K 9/00* | (2006.01) | |
| *A61K 31/56* | (2006.01) | |
| *A61K 47/06* | (2006.01) | |
| *A61K 31/57* | (2006.01) | |
| *A61P 17/00* | (2006.01) | |

(52) U.S. Cl.
CPC ............. *A61K 9/0014* (2013.01); *A61K 31/573* (2013.01); *A61K 31/593* (2013.01); *A61K 47/10* (2013.01); *A61K 2300/00* (2013.01); *A61K 31/56* (2013.01); *A61K 31/59* (2013.01); *A61K 47/06* (2013.01)
USPC ........... 424/484; 424/485; 424/486; 424/487; 424/488; 514/167; 514/178; 514/336; 514/384

(58) Field of Classification Search
None
See application file for complete search history.

(56) References Cited

To view the complete listing of prior art documents cited during the proceeding for Reexamination Control Number 95/000,153, please refer to the USPTO's public Patent Application Information Retrieval (PAIR) system under the Display References tab.

*Primary Examiner* — Evelyn Huang

(57) ABSTRACT

A pharmaceutical composition for dermal use, wherein the composition has a first pharmacologically active component A consisting of at least one vitamin D or vitamin D analogue, and a second pharmacologically active component B consisting of at least one corticosteroid, wherein the difference between the maximum stability pH of said first component A and the maximum stability pH of said second component B is at least 1. The composition can also have at least one solvent component C, where component C is compounds of the general formula $R^3(OCH_2C(R^1)H)_xOR^2$ (I), wherein x is in the range of 2-60, $R^1$ in each of the x units independently is H or $CH_3$, $R^2$ is straight chain or branched $C_{1-20}$alkyl or benzoyl, and $R^3$ is H or phenylcarbonyloxy; di-(straight or branched)-$C_{4-10}$alkyl esters of $C_4$-$C_8$dicarboxylic acids; straight or branched $C_{12-18}$alkyl benzoates; straight or branched $C_{2-4}$-alkyl esters of straight or branched $C_{10-18}$-alkanoic or -alkenoic acids; propylenglycol diesters with $C_{8-14}$-alkanoic acids; and branched primary $C_{18-24}$alkanols.

US 6,753,013 C1

1

INTER PARTES REEXAMINATION CERTIFICATE ISSUED UNDER 35 U.S.C. 316

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 6, lines 14-41:

As a second pharmacologically active component B it is preferred to use a group I, II or III topical steroid, more preferably a medium to weak acting steroid (groups I and II). Component B is preferably selected from the group consisting of Betamethasone (9-fluoro-11,17,21-trihydroxy-16-methylpregna-1,4-diene-3,20-dione) and esters thereof such as the 21-acetate, 17-adamantoate; 17-benzoate, 17-valerate, and 17,21-dipropionate; Alclomethasone and esters thereof such as the dipropionate; [Clobetasole] *Clobetasol* and esters thereof such as the propionate; Clobetasone and esters thereof such as the 17-butyrate; Desoximetasone; Diflucortolon and esters thereof, Diflorasone and esters thereof such as the diacetate; Fluocinonid; Flumetasone and esters thereof such as the pivalate; Fluocinolon and ethers and esters thereof such as the acetonide; Fluticasone and esters thereof such as the propionate; Fluprednidene and esters thereof such as the acetate; Halcinonide; Hydrocortisone and esters thereof such as the -17-butyrate; Mometasone and esters thereof such as the furoate; and Triamcinolon and ethers and esters thereof such as the acetonide; as well as mixtures thereof. More preferred examples of the corticosteroids are Betamethasone or esters thereof such as the 17-valerate or the 17,21-dipropionate, [Clobetasole] *Clobetasol* or esters thereof such as the propionate, Triamcinolon or ethers and/or thereof such as the acetonide or the acetonide-21-N-benzoyl-2-methyl-.beta.-alaninate or the acetonide-21-(3,3-dimethylbutyrate), or Hydrocortisone or esters thereof such as the 17-butyrate.

Column 8, lines 22-41:

As [nor-limiting] *non-limiting* specific examples of the types (i)-(vi) of the solvent component C defined above may be mentioned the following, including trade names:
Arlamol E [(polyoxyethylene(15) stearyl ether)] (*polyoxypropylene-15-stearyl ether*);
Arlamol DoA (diisooctyl ester of adipic acid);
Arlasolve 200 (Polyoxyethylene-20-isohexadecyl ether);
Eutanol G (2-octyldodecanol);
Finsolv (Isostearyl benzoate);
Finsolv P (polyoxypropylene-15-stearyl ether benzoate);
Isopropylesters of straight or branched $C_{10}$-$C_{18}$ alkanoic or alkenoic acids such as isopropyl myristate, isopropyl palmitate, isopropyl isostearate, isopropyl linolate and isopropyl monooleate;
Miglyol 840 (Propylene glycol diester of caprylic and caprinic acid);

2

DPPG (propylene glycol dipelagonate);
Procetyl AWS $(CH_3(CH_2)_{14}CH_2(OCH(CH_3)CH_2)_5$-$(OCH_2)_{20}OH)$.

AS A RESULT OF REEXAMINATION, IT HAS BEEN DETERMINED THAT:

Claims 3, 9, 10, 13, 15, 20 and 22 are cancelled.

Claims 1, 4-5, 7-8, 11-12, 14, 17-19, 21 and 23 are determined to be patentable as amended.

Claims 2, 6 and 16, dependent on an amended claim, are determined to be patentable.

New claims 24-80 are added and determined to be patentable.

1. A pharmaceutical composition for dermal use, said composition comprising:
a first pharmacologically active component A consisting of at least one [vitamin D or] vitamin D analogue selected from the group consisting of seocalcitol, calcipotriol, calcitriol, tacalcitol, maxacalcitol, paricalcitol, falecalcitriol, 1α,24S-dihydroxy-vitamin D2, 1(S),3(R)-dihydroxy-20(R)-[((3-(2-hydroxy-2-propyl)-phenyl)-methoxy)-methyl]-9,10-seco-pregna-5(Z),7(E),10(19)-triene and mixtures thereof; and
a second pharmacologically active component B consisting of at least one corticosteroid, wherein the difference between the maximum stability pH of said first component A and the maximum stability pH of said second component B is at least 1; and
at least one solvent component C selected from the group consisting of:
(i) compounds of the general formula $R^3(OCH_2C(R^1)H)_xOR^2$ (I) wherein x is in the range of 2-60, $R^1$ in each of the x units [independently] is [H or] $CH_3$, $R^2$ is straight chain or branched $C_{1-20}$ alkyl or benzoyl, and $R^3$ is H or phenylcarbonyloxy;
[(ii) di-(straight or branched)-$C_{4-10}$ alkyl esters of $C_4$-$C_8$ dicarboxylic acids;
(iii) straight or branched $C_{12-18}$-alkyl benzoates;
(iv)] (*ii*) straight or branched $C_{2-4}$-alkyl esters of straight or branched $C_{10-18}$-alkanoic or -alkenoic acids;
[(v)propylenglycol] (*iii*) *propyleneglycol* diesters with $C_{8-14}$-alkanoic acids; and
[(vi)] (*iv*) branched primary $C_{18-24}$ alkanols,
*wherein said pharmaceutical composition is storage stable and non-aqueous.*

4. The composition according to claim [3] *2*, wherein said vitamin D analogue is calcipotriol or its hydrate thereof.

5. The composition according to claim 1 or 2, wherein said corticosteroid is selected from the group consisting of Betamethasone, Clobetasol, Clobetasone, [Desoximethasone] *Desoximetasone*, Diflucortolon, Diflorasone, Fluocinonid, Flumethasone, Fluocinolon, Fluticasone, Fluprednidene, Halcinonide, Hydrocortisone, [Mometasone] *Mometasone*, Triamcinolon, and pharmaceutically acceptable esters and acetonides as well as mixtures thereof.

7. The composition according to claim 1 [or 2, wherein said corticosteroid is selected from the group consisting of group I topical steroid, group II topical steroid and group III topical steroid], *wherein said component C is selected from the group consisting of:*
(*i*) *compounds of the general formula* $R^3(OCH_2C(R^1)H)_xOR^2$ (*I*) *wherein x is in the range of 2-60, $R^1$ in each of the x units is $CH_3$, $R^2$ is straight chain or branched $C_{1-20}$ alkyl or benzoyl, and $R^3$ is H or phenylcarbonyloxy;*

(iii) propyleneglycol diesters with $C_{8-14}$ alkanoic acids; and (iv) branched primary $C_{18-24}$ alkanols.

8. The composition according to claim 1 [or 2], wherein [said composition is in the form of a non-aqueous composition] *the amount of component C is from 1% to 20% w/w*.

11. The composition according to claim [10] *1*, wherein said composition [has] *is an ointment having* the following composition:
Betamethasone 0.5 mg
Calcipotriol 50 μg
Paraffin, Liquid 30 mg
Polyoxypropylene-15-Stearyl Ether 50 mg
α-Tocopherol 20 μg
White Soft Paraffin to make 1 g.

12. [A lotion comprising the] *The* composition according to claim 1 [or 2], wherein said component C is selected from the group consisting of isopropyl myristate, propylene glycol dipelagonate and octyldodecanol.

14. The composition according to claim 1, wherein said component C is selected from the group consisting of a compound of the general formula [H(OCH$_2$C(R$^1$)H)$_x$OR$^2$ (II)] $R^3(OCH_2C(R^1)H)_xOR^2$ (*I*) and mixtures thereof, wherein [where] $R^3$ *is H, and* R$^1$, x, and R$^2$ are as defined in claim 1.

17. The composition according to claim 1 [or] containing 0.001-0.25 mg/g or ml of said component A and 0.005-0.1% w/w of said component B.

18. A method of treating psoriasis, sebopsoriasis or seborrhoic dermatitis, the method comprising topically administering an effective amount of the composition of claim 1 [or 2], to a patient in need of such treatment.

19. The method of claim 18, comprising topical administration once [or twice] daily of a medically sufficient dosage of said composition.

21. The method of claim 18, wherein *application of the composition results in a higher efficacy in the treatment of psoriasis, sebopsoriasis or seborrhoic dermatitis than the efficacy attainable when using any composition comprising said components A or B alone, and* the efficacy of said treatment is measured, [and] *wherein said efficacy is measured as* a percentage change in Psoriasis Area and Severity Index score.

23. The pharmaceutical composition of claim [22] *1*, wherein said pharmaceutical composition is stable when stored at 40° C. for 3 months.

24. *A pharmaceutical composition for dermal use, said composition consisting essentially of:*
*a first pharmacologically active component A consisting of at least one vitamin D analogue selected from the group consisting of seocalcitol, calcipotriol, calcitriol, tacalcitol, maxacalcitol, paricalcitol, falecalcitriol, 1α,24S-dihydroxy-vitamin D2, 1(S),3(R)-dihydroxy-20(R)-[(3-(2-hydroxy-2-propyl)-phenyl)-methoxy)-methyl]-9,10-seco-pregna-5(Z),7(E),10(19)-triene and mixtures thereof; and*
*a second pharmacologically active component B consisting of at least one corticosteroid, wherein the difference between the maximum stability pH of said first component A and the maximum stability pH of said second component B is at least 1; and*
*at least one solvent component C selected from the group consisting of:*
   *(i) compounds of the general formula $R^3(OCH_2C(R^1)H)_xOR^2$ (I) wherein x is in the range of 2-60, $R^1$ in each of the x units is CH$_3$, $R^2$ is straight chain or branched $C_{1-20}$ alkyl or benzoyl, and $R^3$ is H or phenylcarbonyloxy;*

*(ii) straight or branched $C_{2-4}$-alkyl esters of straight or branched $C_{10-18}$- alkanoic or -alkenoic acids;*
*(iii) propyleneglycol diesters with $C_{8-14}$-alkanoic acids; and*
*(iv) branched primary $C_{18-24}$ alkanols;*
*wherein said pharmaceutical composition is non-aqueous.*

25. *The composition according to claim 24, wherein said vitamin D analogue is selected from the group consisting of calcipotriol, calcitriol, tacalcitol, maxacalcitol, 1(S),3(R)-dihydroxy-20(R)-[(3-(2-hydroxy-2-propyl)-phenyl)-methoxy)-methyl]-9,10-seco-pregna-5(Z),7(E),10(19)-triene, and mixtures thereof.*

26. *The composition according to claim 24, wherein said vitamin D analogue is calcipotriol or its hydrate thereof.*

27. *The composition according to claim 24, wherein said corticosteroid is selected from the group consisting of Betamethasone, Clobetasol, Clobetasone, Desoximetasone, Diflucortolon, Diflorasone, Fluocinonid, Flumethasone, Fluocinolon, Fluticasone, Fluprednidene, Halcinonide, Hydrocortisone, Mometasone, Triamcinolon, and pharmaceutically acceptable esters and acetonides as well as mixtures thereof.*

28. *The composition according to claim 27, wherein said esters or acetonides are selected from the group consisting of 17-valerate, 17-propionate, 17,21-dipropionate, acetonide, acetonide-21-N-benzoyl-2-methyl-β-alaninate, acetonide-21-(3,3-dimethylbutyrate) and 17-butyrate.*

29. *The composition according to claim 24, wherein said component C is selected from the group consisting of:*
   *(i) compounds of the general formula $R^3(OCH_2C(R^1)H)_xOR^2$ (I) wherein x is in the range of 2-60, $R^1$ in each of the x units is CH$_3$, $R^2$ is straight chain or branched $C_{1-20}$ alkyl or benzoyl, and $R^3$ is H or phenylcarbonyloxy,*
   *(iii) propyleneglycol diesters with $C_{8-14}$ alkanoic acids; and*
   *(iv) branched primary $C_{18-24}$ alkanols.*

30. *The composition according to claim 24, wherein said composition is stable when stored at 40° C. for 3 months.*

31. *The composition according to claim 24, wherein said component C is selected from the group consisting of a compound of the general formula $R^3(OCH_2C(R^1)H)_xOR^2$ (I) and mixtures thereof, wherein $R^3$ is H, and $R^1$, x, and $R^2$ are as defined in claim 24.*

32. *The composition according to claim 31, wherein said component C is polyoxypropylene-15-stearyl ether.*

33. *The composition according to claim 24, wherein said composition contains Betamethasone, calcipotriol, liquid paraffin, polyoxypropylene-15-stearyl ether, α-tocopherol, and white soft paraffin.*

34. *The composition according to claim 24 containing 0.001-0.25 mg/g or ml of said component A and 0.005-0.1% w/w of said component B.*

35. *A method of treating psoriasis, sebopsoriasis or seborrhoic dermatitis, the method comprising*
*topically administering an effective amount of the composition of claim 24 to a patient in need of such treatment.*

36. *The method of claim 35, comprising topical administration once daily of a medically sufficient dosage of said composition.*

37. *The method of claim 35 or 36, wherein application of the composition results in a higher efficacy in the treatment of psoriasis, sebopsoriasis or seborrhoic dermatitis than the efficacy attainable when using any composition comprising said components A or B alone, and the efficacy of said treat-* ment is measured, wherein said efficacy is measured as a percentage change in Psoriasis Area and Severity Index score.

38. A pharmaceutical composition for dermal use, said composition comprising:
   a pharmacologically active amount of calcipotriol or its hydrate thereof;
   a pharmacologically active amount of betamethasone or esters thereof, wherein the difference between the maximum stability pH of calcipotriol or its hydrate thereof and the maximum stability pH of betamethasone or esters thereof is at least 1; and
   at least one solvent component C selected from the group consisting of compounds of the general formula $R^3(OCH_2C(R^1)H)_xOR^2$ (I) wherein x is in the range of 2-60, $R^1$ in each of the x units is $CH_3$, $R^2$ is straight chain or branched $C_{1-20}$ alkyl or benzoyl, and $R^3$ is H or phenylcarbonyloxy;
   wherein said pharmaceutical composition is storage stable and non-aqueous.

39. The composition according to claim 38, wherein said esters of betamethasone are selected from the group consisting of 21-acetate, 17-adamantoate, 17-benzoate, 17-valerate, and 17,21-dipropionate.

40. The composition according to claim 38, wherein $R^3$ is H, and $R^1$, x, and $R^2$ are as defined in claim 38.

41. The composition according to claim 38, wherein said composition is stable when stored at 40° C. for 3 months.

42. The composition according to claim 40, wherein said component C is polyoxypropylene-15-stearyl ether.

43. A method of treating psoriasis, sebopsoriasis or seborrhoic dermatitis, the method comprising
   topically administering an effective amount of the composition of claim 38, to a patient in need of such treatment.

44. The method of claim 43, comprising topical administration once daily of a medically sufficient dosage of said composition.

45. The method of claim 43 or 44, wherein application of the composition results in a higher efficacy in the treatment of psoriasis, sebopsoriasis or seborrhoic dermatitis than the efficacy attainable when using any composition comprising said components A or B alone, and the efficacy of said treatment is measured, wherein said efficacy is measured as a percentage change in Psoriasis Area and Severity Index score.

46. A pharmaceutical composition for dermal use, said composition comprising:
   a pharmacologically active amount of calcipotriol or its hydrate thereof;
   a pharmacologically active amount of hydrocortisone or esters thereof, wherein the difference between the maximum stability pH of calcipotriol or its hydrate thereof and the maximum stability pH of hydrocortisone or esters thereof is at least 1; and
   at least one solvent component C selected from the group consisting of compounds of the general formula $R^3(OCH_2C(R^1)H)_xOR^2$ I wherein x is in the range of 2-60, $R^1$ in each of the x units is $CH_3$, $R^2$ is straight chain or branched $C_{1-20}$ alkyl or benzoyl, and $R^3$ is H or phenylcarbonyloxy;
   wherein said pharmaceutical composition is storage stable and non-aqueous.

47. The composition according to claim 46, wherein said ester of hydrocortisone is 17-butyrate.

48. The composition according to claim 46, wherein $R^3$ is H, and $R^1$, x, and $R^2$ are as defined in claim 46.

49. The composition according to claim 46, wherein said composition is stable when stored at 40° C. for 3 months.

50. The composition according to claim 48, wherein said component C is polyoxypropylene-15-stearyl ether.

51. A method of treating psoriasis, sebopsoriasis or seborrhoic dermatitis, the method comprising
   topically administering an effective amount of the composition of claim 48, to a patient in need of such treatment.

52. The method of claim 51, comprising topical administration once daily of a medically sufficient dosage of said composition.

53. The method of claim 51 or 52, wherein application of the composition results in a higher efficacy in the treatment of psoriasis, sebopsoriasis or seborrhoic dermatitis than the efficacy attainable when using any composition comprising said components A or B alone, and the efficacy of said treatment is measured, wherein said efficacy is measured as a percentage change in Psoriasis Area and Severity Index score.

54. A pharmaceutical composition for dermal use, said composition comprising:
   a pharmacologically active amount of calcitriol;
   a pharmacologically active amount of clobetasol or esters thereof, wherein the difference between the maximum stability pH of calcitriol and the maximum stability pH of clobetasol or esters thereof is at least 1; and
   at least one solvent component C selected from the group consisting of compounds of the general formula $R^3(OCH_2C(R^1)H)_xOR^2$ (I) wherein x is in the range of 2-60, $R^1$ in each the x units is $CH_3$, $R^2$ is straight chain or branched $C_{1-20}$ alkyl or benzoyl, and $R^3$ is H or phenylcarbonyloxy;
   wherein said pharmaceutical composition is storage stable and non-aqueous.

55. The composition according to claim 54, wherein said ester of clobetasol is propionate.

56. The composition according to claim 54, wherein $R^3$ is H, and $R^1$, x, and $R^2$ are as defined in claim 54.

57. The composition according to claim 54, wherein said composition is stable when stored at 40° C. for 3 months.

58. The composition according to claim 56, wherein said component C is polyoxypropylene-15-stearyl ether.

59. A method of treating psoriasis, sebopsoriasis or seborrhoic dermatitis, the method comprising
   topically administering an effective amount of the composition of claim 54, to a patient in need of such treatment.

60. The method of claim 59, comprising topical administration once daily of a medically sufficient dosage of said composition.

61. The method of claim 59 or 60, wherein application of the composition results in a higher efficacy in the treatment of psoriasis, sebopsoriasis or seborrhoic dermatitis than the efficacy attainable when using any composition comprising said components A or B alone, and the efficacy of said treatment is measured, wherein said efficacy is measured as a percentage change in Psoriasis Area and Severity Index score.

62. A pharmaceutical composition for dermal use, said composition comprising:
   a pharmacologically active amount of calcipotriol or its hydrate thereof;
   a pharmacologically active amount of clobetasol or esters thereof, wherein the difference between the maximum stability pH of calcipotriol or its hydrate thereof and the maximum stability pH of clobetasol or esters thereof is at least 1; and at least one solvent component C selected from the group consisting of compounds of the general formula $R^3(OCH_2C(R^1)H)_xOR^2$ (I) range of 2-60, $R^1$ in each of the x units is $CH_3$, $R^2$ is straight chain or branched $C_{1-20}$ alkyl or benzoyl, and $R^3$ is H or phenylcarbonyloxy;

wherein said pharmaceutical composition is storage stable and non-aqueous.

63. The composition according to claim 62, wherein said ester of clobetasol is propionate.

64. The composition according to claim 62, wherein $R^3$ is H, and $R^1$, x, and $R^2$ are as defined in claim 62.

65. The composition according to claim 62, wherein said composition is stable when stored at 40° C. for 3 months.

66. The composition according to claim 64, wherein said component C is polyoxypropylene-15-stearyl ether.

67. A method of treating psoriasis, sebopsoriasis or seborrhoic dermatitis, the method comprising
topically administering an effective amount of the composition of claim 62, to a patient in need of such treatment.

68. The method of claim 67, comprising topical administration once daily of a medically sufficient dosage of said composition.

69. The method of claim 67 or 68, wherein application of the composition results in a higher efficacy in the treatment of psoriasis, sebopsoriasis or seborrhoic dermatitis than the efficacy attainable when using any composition comprising said components A or B alone, and the efficacy of said treatment is measured, wherein said efficacy is measured as a percentage change in Psoriasis Area and Severity Index score.

70. A pharmaceutical composition for dermal use, said composition comprising:
a pharmacologically active amount of calcitriol;
a pharmacologically active amount of betamethasone or an ester thereof, wherein the difference between the maximum stability pH of calcitriol and the maximum stability pH of betamethasone or an ester thereof is at least 1; and
at least one solvent component C selected from the group consisting of compounds of the general formula $R^3(OCH_2C(R^1)H)_xOR^2$ (I) wherein x is in the range of 2-60, $R^1$ in each of the x units is $CH_3$, $R^2$ is straight chain or branched $C_{1-20}$ alkyl or benzoyl, and $R^3$ is H or phenylcarbonyloxy;

wherein said pharmaceutical composition is storage stable and non-aqueous.

71. The composition according to claim 70, wherein $R^3$ is H, and $R^1$, x, and $R^2$ are as defined in claim 70.

72. The composition according to claim 70, wherein said composition is stable when stored at 40° C. for 3 months.

73. The composition according to claim 71, wherein said component C is polyoxypropylene-15-stearyl ether.

74. A method of treating psoriasis, sebopsoriasis or seborrhoic dermatitis, the method comprising
topically administering an effective amount of the composition of claim 70, to a patient in need of such treatment.

75. The method of claim 74 comprising topical administration once daily of a medically sufficient dosage of said composition.

76. The method of claim 74 or 75, wherein application of the composition results in a higher efficacy in the treatment of psoriasis, sebopsoriasis or seborrhoic dermatitis than the efficacy attainable when using any composition comprising said components A or B alone, and the efficacy of said treatment is measured, wherein said efficacy is measured as a percentage change in Psoriasis Area and Severity Index score.

77. The composition according to claim 1, wherein said composition contains a base excipient.

78. The composition according to claim 77, wherein said base excipient is white soft paraffin.

79. The composition according to claim 24, wherein said composition contains a base excipient.

80. The composition according to claim 79, wherein said base excipient is white soft paraffin.

* * * * *